United States Patent [19]

North et al.

[11] Patent Number: 4,882,288
[45] Date of Patent: Nov. 21, 1989

[54] ASSAY TECHNIQUE AND EQUIPMENT

[76] Inventors: John R. North, 2 Cockhall Close, Litlington, Royston, Herts. SG8 0RB; Satham Petty-Saphon, Blythburgh House, Wendens Ambo, Saffron Walden, Essex CB11 4JU; Craig G. Sawyers, 196 Icknield Way, Letchworth, Herts. SG6 4AE, all of United Kingdom

[21] Appl. No.: 866,080
[22] PCT Filed: Sep. 16, 1985
[86] PCT No.: PCT/GB85/00427
    § 371 Date: May 14, 1986
    § 102(e) Date: May 14, 1986
[87] PCT Pub. No.: WO86/01901
    PCT Pub. Date: Mar. 27, 1986

[30] Foreign Application Priority Data

Sep. 14, 1984 [GB] United Kingdom ............... 8423204

[51] Int. Cl.$^4$ ............... G01N 33/553; G01N 33/552; G01N 33/545; G01N 33/577
[52] U.S. Cl. ............... 436/525; 436/527; 436/531; 436/518; 436/548; 436/805; 436/810; 356/305; 356/317; 356/318; 250/461.1; 250/461.2
[58] Field of Search ............... 436/518, 519, 524, 525, 436/526, , 535, 805, 807, 531, 164, 171, 548, 810; 356/317, 318, 417, 305; 250/461.1, 461.2

[56] References Cited

U.S. PATENT DOCUMENTS 4,537,861 8/1985 Elings et al. ............... 436/518
4,647,544 3/1987 Nicoli et al. ............... 436/527

Primary Examiner—Esther M. Kepplinger
Attorney, Agent, or Firm—Merchant, Gould, Smith, Edell, Welter & Schmidt

[57] ABSTRACT

An assay technique for the qualitative and/or quantitative detection of a chemical, biochemical or biological species in a sample comprising (a) coating at least a predetermined part of a pre-formed surface with a thin film of a material capable of binding the species to be assayed, said thin film incorporating a fluorescent compound whose fluorescent properties show a dependence upon it's molecular environment and said surface being optically active with respect to radiation over a predetermined band of wavelengths (b) contacting the coated surface with the sample and (c) measuring the change in fluorescent properties of said fluorescent compound before and after binding of said species. The preformed surface is preferably a diffraction grating.

25 Claims, 2 Drawing Sheets

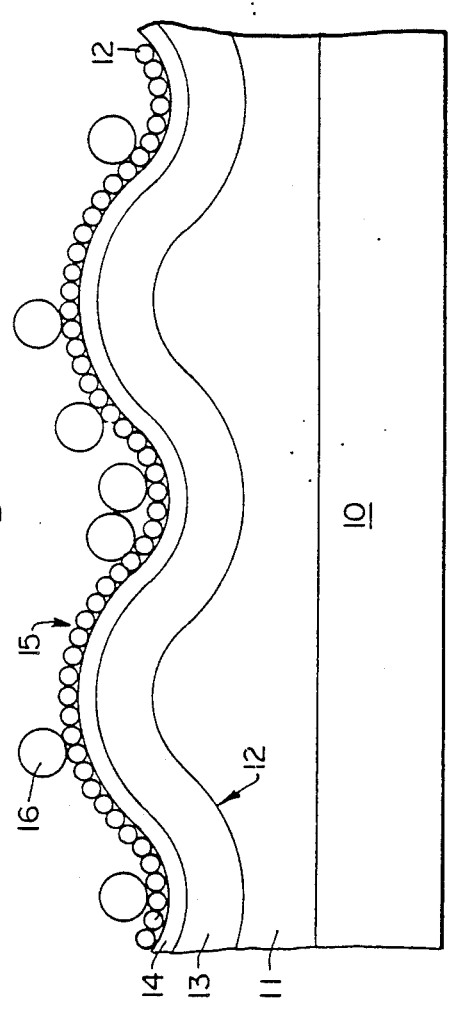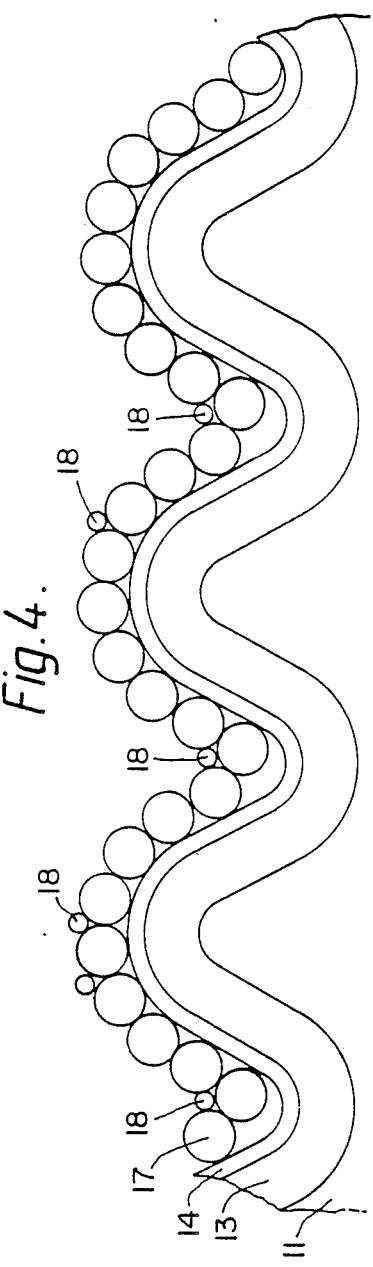

ASSAY TECHNIQUE AND EQUIPMENT

This invention relates to an assay technique for qualitative and/or quantitative detection of chemical, biochemical or biological species in a sample and to apparatus and equipment for use in such a technique The technique is based, upon the affinity of the species which is to be assayed for a receptive material, for example a ligand or a specific binding partner, which receptive material is coated onto a particular type of surface.

Our International Pat. Publication No. WO84/02578 describes and claims an assay technique for qualitative and/or quantitative detection of a chemical, biochemical or biological species in a sample, which comprises (a) coating at least a predetermined part of a surface having a pre-formed relief profile on a substrate with a thin film of a material capable of binding the species to be assayed, said surface part being optically active with respect to radiation at least over a predetermined band of wavelengths; (b) contacting the coated surface with the sample; and (c) observing the optical properties of said surface part in order to determine a qualitative and/or quantitative change in optical properties as a result of the binding of the species onto said thin film of material The same publication also describes and claims an article for use in such an assay technique, the article comprising a substrate having a surface with a pre-formed relief profile which is optically active with respect to radiation at least over a predetermined band of wavelengths, and at least a predetermined part of which surface is coated with a thin film of a material capable of binding a predetermined chemical or biochemical or biological species. The substrate is most preferably a lamellar plastics material and may conveniently be in strip-form The pre-formed surface relief profile may take a variety of forms, but broadly speaking the profile may be referred to as a grating It may consist of a single grating or of two or more crossed gratings The grating profile may be square-wave, sinusoidal or saw-tooth, for example; it may also be derived from the arrangement of a series of protuberances formed on the surface.

It will be convenient hereinafter to use the term "grating" to refer to a surface with a pre-formed relief profile of the type disclosed in our International Pat. Publication WO84/02578. It will be appreciated that the surface which constitutes the grating may be of the same material as the substrate itself, or it may be of a different material (in which case the substrate will carry said different material)

Our International Pat. Publication No WO84/02578 discloses an invention of which a key characteristic is the use of a grating in an assay technique It effectively marries the optical effects which may be achieved using gratings with the chemical or biochemical techniques used in molecular assays in order to improve such assays The disclosure of International Pat. Publication No. WO84/02578 is incorporated herein by reference thereto Our present understanding of the mechanistic aspects of this earlier invention is that the change in optical properties of the article as a result of the binding of a species to be assayed (e.g. a specific antigen in blood serum) is brought about essentially as a result of (i) the mass or bulk of bound molecules and (ii) their dielectric properties. Sensitivity however will depend on the size of the antigen molecule concerned: more small molecules will need to be bound than large molecules in order to produce the same change in optical properties (assuming the dielectric properties of the different molecules are unchanged). Although the technique of this earlier invention constitutes a considerable advance in the art, nevertheless this dependence on molecular size and dielectric properties does limit the application of the technique. The present invention aims to overcome or ameliorate this limitation of the earlier invention.

Because surface phenomena greatly affect both the physical and the chemical aspects of a measuring technique involving the use of active molecules attached to a grating surface, it is not possible to predict, a priori, how an article as described and claimed in our International Pat. Publication No. WO84/02578 would behave if it were modified by the incorporation of additional molecules into the thin film of material which is capable of binding the species to be assayed. After extensive investigations, we have now found, surprisingly, that very large increases in measurement sensitivity can be achieved if the active layer (i.e. the thin film of material capable of binding the species to be assayed) formed over the grating is tagged with a fluorescent molecule; furthermore, the sensitivity of the system is much less dependent on the size or bulk of the bound molecules and on their dielectric properties. Accordingly, in one aspect of the present invention, there is provided an article for use in an assay technique for qualitative and/or quantitative detection of a chemical, biochemical or biological species in a sample, which article comprises a substrate having or carrying a surface with a pre-formed relief profile which is optically active with respect to radiation at least over a predetermined band of wavelengths, and at least a predetermined part of which surface is coated with a thin film of a material capable of binding a predetermined chemical or biochemical or biological species, said thin film of material incorporating molecules of a fluorescent compound whose fluorescent properties show an observable dependence upon its molecular environment.

The pre-formed relief profile is preferably a grating. A single grating may be employed, or the surface may comprise two or more gratings disposed mutually at an angle. Where there are two such gratings, they may be mutually orthogonal The profile of the or each grating is advantageously square-wave or sinusoidal. Sinusoidal gratings are presently preferred. Saw-tooth profiles are also possible, but are not presently preferred.

The pre-formed relief profile may alternatively comprise a regular array of protuberances. With a surface of this type, the alignment of the peaks of the protuberances and the troughs between the protuberances corresponds to the ridges and troughs of a grating-type structure.

A monomolecular layer of the receptive material will suffice and will generally be preferred.

The pre-formed relief profile may be present at the surface of the substrate, or at the surface of a layer carried by the substrate.

Conveniently, the substrate is formed of a plastics material. A presently preferred plastics material is polymethylmethacrylate. An alternative substrate is a glass coated with a synthetic polymeric material. Where the pre-formed relief profile is generated in a plastics material, then plastics materials curable by ultra-violet light are preferred, and in particular acrylic or polyester materials can advantageously be used; the plastics material preferably has a refractive index in the range 1.25 to 1.6, and more preferably a refractive index of about 1.4.

The active surface of the article (i.e., that surface which is, or which carries, the pre-formed surface) will generally be constituted by a metal or a metal layer. Thus a plastics substrate, e.g., of polymethylmethacrylate, can have adhering thereto a layer of a UV-curable polyester material in which the desired relief profile is generated; and a thin metal layer which conforms to the pre-formed relief profile (e.g. a single grating structure of depth about 30 nanometers and period about 600 nanometers) adheres thereto. The plastics/metal interface may alternatively be planar: In which case the desired relief is generated directly in the metal.

Generally, the substrate will be lamellar. It may be in strip-form.

The grating structure adopted for an article in accordance with the present invention is preferably a metallised shallow grating i.e. a diffraction grating having a depth (peak-to-trough) of up to 400 nanometers, preferably of from 30 to 100 nanometers, and a pitch (period) which is greater than the grating depth and is generally in the range from 400 to 2000 nanometers. The overcoating metal layer is preferably of silver or aluminium and has a thickness of up to 500 nanometers, preferably 100 plus or minus 10 nm. Less preferred overcoating metals are gold and copper. Ideally, the metal layer should be highly reflecting at both the absorption (i.e. dye excitation) wavelength and at the fluorescence wavelength. A passivation or capping layer of, for example, an oxide of silicon or of aluminium may advantageously coat the metal itself.

A dye molecule or residue may be bound to the active layer so that the dye molecule or residue is remote from the metallised grating surface. Alternatively, a dye molecule or residue may be bound directly to the surface of the metallised grating and the active layer, e.g. of antigen, may then be bound to the dye molecule. With either arrangement, the dye (fluorochrome) to metal distance is preferably 10 nm or more in order to optimise absorption of incident radiation by the dye molecule or residue.

The binding of the active layer to the grating and of the dye (fluorochrome) to the grating and/or to the active layer is effected by conventional techniques which do not themselves form a part of the present invention.

If desired, a dye molecule or residue which is to be incorporated into the surface structure of an article in accordance with this invention may incorporated in a phospholipid layer in order to control the surface distribution and concentration of dye molecules in the resultant article.

The dye or dyes for use in an article in accordance with this invention preferably absorb strongly at the emission wavelength of a suitable laser which may thus constitute the excitation source. Examples of suitable layers are: Argon ion (488 nm); HeNe (543 nm); frequency doubled YAG (532 nm); and frequency tripled YAG (355 nm). Sources such as these are known per se and their design and construction does not of itself form a part of the present invention. The dyes used will generally absorb in the blue/green parts of the visible spectrum and will flucresce in the green/red/infrared. Typically, dyes of the coumarin, rhodamine or fluorescein families, or the ion $Eu^{+++}$, will be used.

In a preferred embodiment of an article in accordance with this invention, the dye may be located in a sensitive molecular environment which is such that fluorescence is quenched after binding of the species undergoing assay but is activated in the absence of such species; the reverse arrangement—i.e. in which binding of the species activates fluorescence, which is otherwise quenched by the molecular environment of the dye—is equally preferred. In these embodiments, a single measurement taken after the article has been subjected to the species undergoing assay may suffice, after appropriate calibration, to determine the quantity of species present in the sample.

According to another aspect of the present invention, there is provided an assay technique in which an article as hereinbefore defined is subjected to a fluid containing the species to be assayed, said thin film of material carried by the article being selected in accordance with the species to be assayed, wherein a comparison is made between the fluorescent properties of said dye molecule after and before binding of the species undergoing assay. Preferably, incident radiation is directed at the surface of said article at a predetermined angle of incidence and at a wavelength which is (a) such as to excite the dye molecule into the fluorescent state, and (b) such as to be resonant with the grating surface structure, thus effecting substantially complete absorption of the incident radiation. Similarly, observation of the fluorescent emission from the dye molecules is preferably carried out at a predetermined angle of emission, which may be that at which maximum fluorescence occurs either (i) in the absence of, or (ii) in the presence of, the species undergoing assay.

For ease of illustration, let us suppose that the article is a lamellar plastics material carrying a single grating which is coated with a mono-molecular (or approximately mono-molecular) layer of a preselected antibody. The antibody molecule is tagged with a fluorescent dye by conventional chemical techniques. If this article is now used to carry out an assay for the antigen corresponding to the bound antibody, radiation (generally light) may be introduced at a first wavelength and at an angle of incidence which is resonant with the grating structure so that substantially total absorption of the light occurs. Because of the proximity of the dye molecule to the grating, this results in very strong absorption of the incident radiation by the dye molecule. Conventional considerations would lead us to believe that the fluorescent material would re-radiate at its fluorescent wavelength uniformly in all directions. The grating surface, however, is found to have a dramatic effect upon the fluorescent behaviour of the dye; it is believed that the grating surface induces a plasmon surface wave which interacts with the dye molecule. The result is that the fluorescence is emitted at a specific angle with respect to the surface of the grating rather than uniformly over all angles. We have thus found that strongly directed fluorescence results from absorption of the incident radiation, given that the angle of incidence of the radiation and its wavelength are selected appropriately. If now the antigen for which the assay is being performed becomes bound to the antigen layer with its associated dye molecules, the molecular environment of the dye molecules is altered. We have found that this alteration of the molecular environment of the dye molecules results in lower absorption of incident radiation, probably because the extra molecular material attached over the grating surface acts as a dielectric layer of increased thickness, thereby shifting the absorption resonance. This means that the angle of incidence required for maximum absorption of incident radiation is altered by the presence of the antibody molecules and therefore if the incident radiation is still directed at the article at its original angle of incidence, the absorption by the dye molecules is considerably reduced. This in turns means that the amount of fluorescent radiation exiting from the grating structure is also reduced. Furthermore, the increased thickness of dielectric material over the grating surface reduces the coupling between the plasmon surface wave and the dye molecule with a result that the angle of emission of fluorescent radiation is broadened. Thus observations of the fluorescent radiation at the original angle of emission of fluorescence (i.e. that for maximum intensity in the absence of antibodies) will show, when antibodies are bound, a very sharp reduction in intensity. In the extreme case, fluorescence will be quenched altogether. Thus a very sensitive monitoring and measuring technique is available. The technique described in this paragraph is a fluorescence—inhibition technique; this is useful where higher concentrations of analyte are being detected.

An alternative approach to the measuring technique may be adopted and, in some circumstances, may be of particular advantage. In this alternative arrangement, the angle of incidence of radiation is set at a value different from that which couples most effectively with the grating surface structure, but such that increase of the thickness of dielectric over the grating due to binding of the species being assayed causes the angle of incidence to approach, and ultimately to equal, that at which maximum absorption occurs. With this arrangement, it will be appreciated that binding of the species undergoing assay will result in an increase in absorption of incident radiation, rather than a decrease, and consequently in an increase in fluorescent emission, rather than a decrease. Also, since the fluorescence phenomenon is susceptible to the molecular environment of the dye molecule, it is possible to have zero fluorescence (i.e. quenching) in the article before binding of, say, antigen—fluorescence then being activated by binding of the antigen to the surface of the article. This represents the extreme of the case under consideration. The angle of incidence of radiation may be chosen such that maximum fluorescence is observed at the chosen angle of emission when the proportion of species undergoing assay in the fluid with which the article is contacted has a specific value. Thus increasing the amount of, for example, antibody in a saline carrier from zero will initially cause the fluorescent emission to increase up to a maximum after which further increase in the antibody content will result in fluorescence intensity decreasing once more. This approach to measurement may be of particular value in the quality control of biologically active fluids since the angle of incidence may be set to give maximum fluorescent emission at the desired concentration of the biologically active ingredient, whereupon any significant deviation from the predetermined concentration will show up as a decrease in fluorescent emission.

The technique described in the preceding paragraph is a fluorescence-activation technique, and this is particularly effective in determining the presence of very small amounts of the species undergoing assay (i.e. the analyte).

With techniques such as those described above, it is possible, instead of measuring the intensity of the fluorescent emission, to observe the lifetime of the dye in its excited state. Conventionally, the half-life of the excited state is termed T. The environment of a fluorescent molecule has a marked effect upon the value of T. Thus the spacing of the dye molecule from the grating surface will affect T, as will the uniformity of the surface structure. Provided the structure is regular, as will generally be the case, we have found that it is possible to observe the effect of a species being bound to, say, an antigen layer carrying a fluorescent dye tag without any obscuration of the observed effect owing to altered distances from species to grating. A practical application of this technique is to observe the fluorescent intensity after a predetermined time has elapsed after the input of incident radiation. The incident radiation may be continuous until it is switched off, or it may be pulsed. Typically, observations may take place about 500 nanoseconds after cessation of input radiation. By choosing the angle of incidence of the incident radiation and the angle of observation of emitted fluorescence in the ways described hereinbefore, a measurement taken after a predetermined time lapse following cessation of radiation input will give an even more sensitive measuring technique, since the addition of, say, an antibody molecule to the dye-tagged antigen results in the lifetime of the excited state of the dye molecule being shortened. Thus the decrease in fluorescent intensity observed after the binding of antibody is even greater than would be observed with steady state incident radiation and fluorescence.

In a modification of the assay technique of this invention, the dye tag is attached to the species undergoing assay, rather than being incorporated in the article onto which the sample is contaced. Examination of the article after contact with the sample gives an indication of the presence or absence of the analyte since the article will exhibit some degree of fluorescence as a result of binding the analyte.

A major benefit of any assay technique involving fluorescence phenomena is that observations and measurements are taken at a wavelength different from that of the input radiation: hence there is no difficulty in distinguishing between input and output radiation. In addition, while it will generally be convenient to work with a layer of active material which is mono-molecular, and with each molecule carrying a dye-tag, deviation from these ideal conditions does not seriously disrupt the validity of the measuring techniques described, although in the embodiment which takes advantage of changes in the half-life of the excited state, lack of uniformity in the article used is more undesirable. No difficulties arise with steady state measurements.

The techniques of this invention work adequately when the article is immersed in a suspension or solution of the species undergoing assay. Thus measurements can take place, for example, with the assayed species in aqueous solution. The incident radiation can be introduced either through the solution itself (i.e. from above) or through the substrate of the article (i.e. from beneath). Likewise, it is possible to observe the emitted radiation from above or from below. It will be appreciated that, where incident radiation is directed at rear the surface of the substrate, the metal coating layer over the grating must be sufficiently thin to allow the plasmon field to pass therethrough.

Compared to conventional fluorescence systems, the present invention provides several advantages:

(1) In conventional systems, the fluorochrome is free to radiate over all angles. In the present invention, the dye molecule couples via the surface plasmons into a narrow cone of angles, thereby enhancing detection sensitivity at the emission angle.

(2) The resonant coupling between radiating fluorochrome and surface plasmon reduces the fluorescent lifetime of the molecule. This enables more excitation-emission cycles to be performed per unit time, leading to increased emitted fluorescent power as compared with an equal number of free dye molecules.

(3) In conventional liquid-phase fluorescence immuno-assay, the beam of light at the excitation wavelength is diffused over the whole sample volume; the number of photons per second available to interact with each fluorochrome is limited. In the present invention, the light is concentrated via the surface plasmon excitation to a high-intensity, very narrow region in the vicinity of the metallised grating surface. The probability of a fluororchrome-interacting is therefore much higher thereby enhancing excitation efficiency.

Although reference has been made in the present description to a layer of antigen molecules as the active layer overcoating the grating surface, it will be appreciated that binding partners of other types may be used, the choice being determined in each case by the nature of the species which is to be assayed. Further, where the active binding material is of biochemical or biological origin, it is not essential to use a complete molecule, e.g. antigen molecule; the active fragment of the total antigen is adequate for the purposes of the present assay arrangements. Similarly, it is not essential for the entire molecular structure of a given dye to be bound to the antigen or antigen fragment; again, the active dye residue is sufficient.

For a better understanding of the invention, and to show how the same may be carried into effect, reference will now be made, by way of example, to the accompanying drawings, in which:

FIG. 3 illustrates schematically a cross-section of an article in accordance with the invention; and FIG. 4 illustrates schematically a second article in accordance with the invention.

Figure 1:
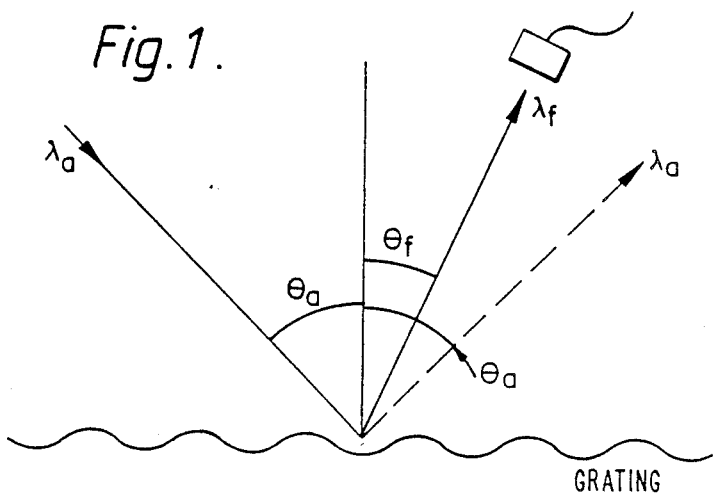
FIG. 1 illustrates one measurement technique in accordance with this invention.

Referring to FIGS. 1 and 2, a beam of light whose wavelength corresponds to the absorption wavelength of the dye molecules is incident on a diffraction grating at an angle which generates the maximum surface plasmon response. Fluorescence, at wavelength $\lambda_f$, when present, is emitted at an angle $\theta_f$.

The angles of absorption and emission are determined by the relationship:

$$\lambda_f \sin\theta_a = \lambda_a \sin\theta_f$$

Figure 2A:
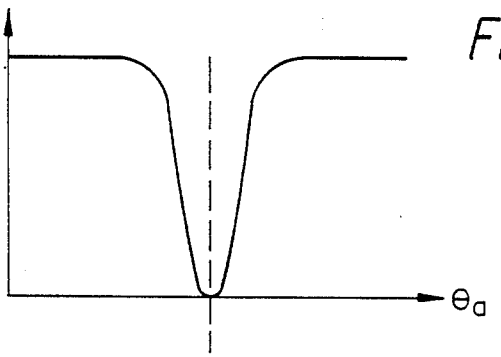
FIG. 2a shows how the reflected power at the absorption wavelength varies as a function of the angle of incidence of excitation radiation.
Figure 2B:
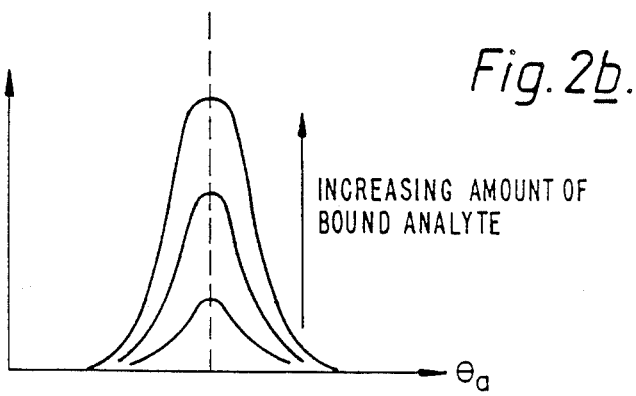
FIG. 2b shows how the reflected power at the fluorescent wavelength varies with angle of incidence of excitation radiation and with the amount of bound analyte.

When the analyte molecule is sufficiently small that binding does not measurably affect the resonance angles, the reflected power at the absorption and fluorescent wavelengths varies as a function of incident angle in the manner shown in FIGS. 2a and 2b. The reflected power at the absorption wavelength behaves in the usual way for plasmon resonance. The reflected power at the fluorescent wavelength increases as the amount of bound analyte increases, and the maximum in the curve occurs at the angle of incidence which excites the maximum plasmon resonance.

Referring next to FIG. 3, an article in accordance with this invention is shown in the condition after it has been contacted by a sample in the method of the invention. The article comprises a substrate 10 formed of polymethylmethacrylate which is about 1 millimeter thick. The substrate carries a polyester layer 11 which carries the pre-formed relief profile 12. The active surface of the article comprises a layer 13 of aluminium of thickness 20 nanometers which conforms, at its upper surface, to relief profile 12. This layer is covered by a passive film 14 of aluminium oxide (thickness 10 nanometers or less) which also conforms to profile 12. A monomolecular layer of antigen molecules 15 is covalently bonded to the film 13 of aluminium oxide and is thus immobilised. The antigen molecules 15 are tagged with the fluorescent dye Rhodamine B. A monomolecular discontinuous layer of antibodies 16 is attached to the antigen layer 15. The substrate 10 with the layers 11, 13, 14 and 15 constitutes one embodiment of the article of this invention. The pre-formed relief profile is in the form of a single sinusoidal grating of depth (peak-to-trough) 30 nanometers and of pitch (period) 600 nanometers. The pitch, which is regular across the surface of the article, is shown compressed for ease of depiction. The article is observed, in carrying out the method of the invention, with monochromatic light which is polarised in a plane perpendicular to the lines of the grating; the angle of incidence of the illumination (from a HeNe) laser was selected to give maximum plasmon resonance. In the absence of antibodies 16, i.e. before contact between the article and the sample, fluorescence of the fluorochrome was strongly activated and was emitted in a narrow cone, rather than uniformly. Increasing numbers of antibody molecules 16 result in progressive quenching of the fluorescence.

Referring next to FIG. 4, there is shown part of a second type of article in accordance with this invention. The layers 11, 13 and 14 are identical to those described above in relation to FIG. 3. Layer 17 is a bound layer of antibody molecules, to which a number of antigen molecules 18 have become attached after contact between the article and a sample for assay. The sample containing antigen molecules 18 (analyte) was previously treated (by conventional techniques) to dye-tag the molecules 18. Because of the plasmon coupling effect described hereinbefore, fluorescence of the discontinuous monomolecular layer 18 can be observed even when very few molecules 18 are present. This enables a very sensitive means of assaying the antigen molecules 18. It is possible to observe this fluorescence even in the presence of other components of the sample and unattached antigen molecules.

In FIG. 3, the layer 16 is monomolecular, with a coverage of about ten percent of the surface, for example. With molecules of about ten nanometers in height, this is equivalent to a mean layer thickness of about one nm.

We claim:

1. An article for use in an assay technique for qualitative and/or quantitative detection of a chemical, biochemical or biological species in a sample, which article comprises a substrate having a surface with a pre-formed relief profile which is optically active with respect to radiation at least over a predetermined band of wavelengths, and at least a predetermined part of which surface is coated with a thin film of a material capable of binding a predetermined chemical or biochemical or biological species, said thin film of material incorporating molecules of a fluorescent compound whose fluorescent properties show an observable dependence upon its molecular environment.

2. An article as claimed in claim 1, wherein the substrate is a plastic material.

3. An article as claimed in claim 2, wherein said plastic material is a material which is curable by ultra-violet light.

4. An article as claimed in claim 2 wherein said plastic material is an acrylic or a polyester material.

5. An article as claimed in claim 2, wherein said plastic material is polymethylmethacrylate.

6. An article as claimed in claim 1, wherein the substrate is a glass coated with a synthetic polymeric material.

7. An article as claimed in claim 1 wherein the substrate is lamellar.

8. An article as claimed in claim 7, wherein the substrate is in strip-form.

9. An article as claimed in claim 6, wherein the pre-formed surface relief profile is in the form of one or more gratings, with two or more gratings disposed mutually at an angle.

10. An article as claimed in claim 9, wherein the or each grating is of square-wave, sinusoidal or saw-tooth profile.

11. An article as claimed in claim 6, wherein the pre-formed surface relief profile comprises a regular array of protuberances.

12. An article as claimed in claim 1, wherein said surface is constituted by a metal or a metal layer.

13. An article as claimed in claim 12, wherein the metal is silver or aluminium.

14. An article as claimed in claim 12, wherein the metal is copper or gold.

15. An article as claimed in claim 13, wherein the metal is coated with a layer of an oxide of silicon or aluminium.

16. An article as claimed claim 1, wherein said thin film of material comprises specific antigens or antibodies, tagged with a fluorescent compound.

17. An article as claimed in claim 16, wherein said antibodies are monoclonal antibodies.

18. An article as claimed in claim 16, wherein said fluorescent compound is a dye of the coumarin, rhodamine or fluorescein or is the ion $Eu^{+++}$.

19. An article as claimed in claim 1, wherein the molecular environment of said fluorescent compound is such that fluorescence is activated before said species is bound to the article and quenched or partially quenched after said species is bound to the article, or vice versa.

20. An assay technique for qualitative and/or quantitative detection of a chemical, biochemical or biological species in a sample which comprises:
(a) coating at least a predetermined part of a surface having a pre-formed relief profile which is optically active with respect to radiation at least over a predetermined band of wavelengths, with a thin film of a material capable of binding the species to be assayed, said thin film of material incorporating molecules of a fluorescent compound whose fluorescent properties show an observable dependence upon its molecular environment;
(b) contacting the coated surface with the sample; and
(c) measuring the change in fluorescent properties of said fluorescent compound after and before binding of the species undergoing assay whereby said change in fluorescent properties provides a qualitative and/or quantitative detection of the species to be assayed.

21. A method as claimed in claim 20, in which incident radiation is directed at the surface of said article at a predetermined angle of incidence and at a wavelength which is (a) such as to excite the dye molecule into the fluorescent state, and (b) such as to be resonant with the grating surface structure.

22. A method as claimed in claim 21, wherein observation of the fluorescent emission from the dye molecules is carrried out at a predetermined angle of emission which is that at which maximum fluorescence occurs in the absence of the species undergoing assay.

23. A method as claimed in claim 21, wherein observation of the fluorescent emission from the dye molecules is carried out at a predetermined angle of emission which is that at which maximum fluorescence occurs in the presence of the species undergoing assay.

24. A method as claimed in claim 20, in which the fluorescent compound is incorporated into the species to be assayed, instead of into said thin film.

25. In an assay technique for the qualitative and/or quantitative detection of a chemical, biochemical, or biological species in a sample comprising measuring the change in optical properties of a substrate having a surface with a pre-formed relief profile, wherein said change in optical properties occurs as a result of the binding of said species to a thin film of material capable of binding said species said thin film being coated over at least a pre-determined part of said surface, the improvement wherein a fluorescent compound is present at said surface and the fluorescent properties are the optical properties which are measured to provide the qualitative and/or quantitative detection of said species.

* * * * *

UNITED STATES PATENT AND TRADEMARK OFFICE
CERTIFICATE OF CORRECTION

PATENT NO. : 4,882,288  Page 1 of 2

DATED : November 21, 1989

INVENTOR(S) : John R. North, Satham Petty-Saphon, Craig G. Sawyers

It is certified that error appears in the above-identified patent and that said Letters Patent is hereby corrected as shown below:

Title page, "§ 371 Date, and § 102(e) Date" should be --May 13, 1986--

Col. 1, line 7
    after "technique" insert a period line 27
    after "material" insert a period line 37
    after "strip-form" insert a period line 39
    after "grating" insert a period line 40
    after "gratings" insert a period line 51
    after "material)" insert a period line 52
    after "No" insert a period line 58
    after "says" insert a period line 60
    after "thereto" insert a period Col. 1, line 8
    delete the comma Col. 2, line 46
    after "orthogonal" insert a period

UNITED STATES PATENT AND TRADEMARK OFFICE
CERTIFICATE OF CORRECTION

PATENT NO. : 4,882,288

DATED : November 21, 1989

INVENTOR(S) : John R. North, Satham Petty-Saphon, Craig G. Sawyers

It is certified that error appears in the above identified patent and that said Letters Patent is hereby corrected as shown below:

Col. 3, line 50
    after "may" insert --be--

Col. 3, line 64
    "flucresce" should be --fluoresce--

Col. 5, line 49
    "fluorescnt" should be --fluorescent--

Col. 6, line 32
    "contaced" should be --contacted--

Col. 7, line 17
    "fluororchrome" should be --fluorochrome--

Col. 9, line 44
    after "claimed" insert --in--

Col. 10, line 49
    after "species" insert a comma

Signed and Sealed this

Twenty-fifth Day of June, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO.   :   4,882,288

DATED        :   May 13, 1986

INVENTOR(S)  :   John R. North, Satham Petty-Saphon, Craig G. Sawyers

It is certified that error appears in the above-identified patent and that said Letters Patent is hereby corrected as shown below:

In Column 10, lines 26, 30 and 35:
    In claims 21, 22 and 23 change "dye" to --fluorescent--.

Signed and Sealed this

Seventeenth Day of September, 1991

*Attest:*

HARRY F. MANBECK, JR.

*Attesting Officer*    *Commissioner of Patents and Trademarks*